United States Patent [19]

Carew

[11] Patent Number: 5,123,901
[45] Date of Patent: Jun. 23, 1992

[54] METHOD FOR SEPARATING PATHOGENIC OR TOXIC AGENTS FROM A BODY FLUID AND RETURN TO BODY

[76] Inventor: E. Bayne Carew, 23131 Lodge La., Dearborn, Mich. 48124

[21] Appl. No.: 160,129

[22] Filed: Feb. 25, 1988

[51] Int. Cl.$^5$ ............................................. A61M 37/00
[52] U.S. Cl. ........................................... 604/5; 604/6; 435/174; 436/806
[58] Field of Search ..................... 604/5, 6; 435/174; 436/806

[56] References Cited

U.S. PATENT DOCUMENTS

| | | | |
|---|---|---|---|
| 3,970,518 | 7/1976 | Giaever | 435/29 |
| 4,381,004 | 4/1983 | Babb | 604/5 |
| 4,634,417 | 1/1987 | Korec | 604/6 |
| 4,664,796 | 5/1987 | Graham . | |
| 4,666,595 | 5/1987 | Graham . | |
| 4,677,067 | 6/1987 | Schwartz | 436/806 |

FOREIGN PATENT DOCUMENTS

84/01503 4/1984 PCT Int'l Appl. .

OTHER PUBLICATIONS

Graham—Chem. Abst., vol. 101, (1984), p. 86920p.
"Magnetic Affinity Chromatography: An Emerging Technique", E. T. Menz et al.
"Immunomagnetic Purging and Autologous Transplantation in Stage D Neuroblastoma", *Antibody-Mediated Methods*, pp. 89-93.
"Immunomicrospheres: Reagents for Cell Labeling and Separation", A. Rembaum et al., *Science*, vol. 308, Apr. 25, 1980.
"T Lymphocyte Depletion of Human Peripheral Blood and Bone Marrow Using Monoclonal Antibodies and Magnetic Microspheres", A. P. Gee et al., *Bone Marrow Transplantation*, (1987), 2, 155-163.
"Affinity Chromatography for Cell Separation: Mathematical Model and Experimental Analysis", Daniel A. Hammer et al., *Biotechnology Progress*, (vol. 3, No. 3), Sep., 1987, 189-204.

*Primary Examiner*—Sam Rosen
*Attorney, Agent, or Firm*—Dykema Gossett

[57] ABSTRACT

A method for removing or separating pathogenic or toxic agents from body fluids is provided. In substance, a fluid containing a preselected pathogenic or toxic agent is flowed into a mixing coil along with a plurality of paramagnetic beads. The paramagnetic beads include a coating which selectively binds the preselected pathogenic agent. By generating a magnetic field, the paramagnetic beads having the bound pathogenic agent are magnetically separated from the fluid. In one embodiment, the method includes the separation of HIV virus and/or HIV infected T-lymphocyte cells from blood. A continuous flow device for implementing the method of the present invention is also provided which includes in one embodiment a peristaltic pump which moves the subject liquid and paramagnetic beads through a mixing coil to promote contacting and binding of the paramagnetic bends to the pathogenenic agent. A magnetic separator in flow communication with the mixing coil is provided by which a magnetic field is generated which causes the paramagnetic beads with bound pathogenic agent to adhere magnetically to the wall of the separator. The method and apparatus of the present invention are particularly useful for the continuous purging of a preselected pathogen from the blood of a human subject.

2 Claims, 2 Drawing Sheets

METHOD FOR SEPARATING PATHOGENIC OR TOXIC AGENTS FROM A BODY FLUID AND RETURN TO BODY

FIELD OF THE INVENTION

The present invention relates generally to the separation of a preselected substance from a fluid. More specifically, the present invention relates to a method and apparatus for removing pathogenic or toxic agents from a biological fluid.

BACKGROUND OF THE INVENTION

For many years, chromatographic and filter separation systems have been used to isolate one or more components of a multi-component sample. For example, liquid chromatography devices typically include a column which is packed with a solid absorbent that selectively retards the movement of sample components through the column. Chromatography has been used widely for the separation of closely related organic compounds and is an indispensable step in most chemical analysis. More recently, affinity chromatography and filtration devices have evolved which utilize highly specific complimentary binding sites on the stationary and mobile phases. These systems have been used successfully for the separation and purification of biological macromolecules.

Affinity chromatography and filtration techniques now exist which can be used to selectively bind and separate complex biological materials such as cells. Typically, polyclonal or monoclonal antibodies which selectively bind to an antigenic determinant or epitope on the surface of the target cell are produced using immunization and purification techniques which will be known to those skilled in the art. The purified antibodies are then immobilized on a solid substrate which can be packed into a column or the like. A suspension containing the target cell population is then flowed through the column whereby the immobilized antibodies selectively recognize and bind the complimentary cell-surface antigen. Thus, the target cells are retained in the column, bound to the immobilized antibodies. If desired, the bound target cells may than be eluted using a suitable carrier.

It is also known that magnetic or paramagnetic beads can be coated with antibodies which selectively bind complex biological materials such as viruses and cells. The coated beads or microspheres are then used to separate and isolate a preselected component from a mixture. For example, in copending U.S. patent application Ser. No. 113,589 filed Oct. 27, 1987, which has been assigned to the assignee of the present invention, the use of paramagnetic microspheres which are coated with antibodies that selectively bind T-lymphocyte cells is disclosed in a novel detection method. In substance, T-lymphocytes are separated from a whole blood sample by placing the sample in a test tube or the like along with antibody-coated paramagnetic beads. A bond then forms between the antibody coating and the T-lymphocytes. Using a magnetic field generator, a magnetic field is generated which causes the paramagnetic microspheres to which the T-cells are attached to adhere to the walls of a test tube. Other blood constituents may then be removed simply by aspirating the contents of the tube while the paramagnetic microspheres and the attached T-cells remain magnetically adhered to the tube walls. This separation technique is used to isolate a specimen in which a pathogen can then be detected. In one embodiment, the aforementioned detection method is utilized to detect the presence of the virus responsible for autoimmune deficiency syndrome (AIDS).

In recent years, the proliferation of certain diseases in man and animals such as AIDS has stimulated intense research efforts to develop an effective vaccine and treatment. While the aforementioned detection method provides a rapid and accurate method of detecting AIDS, current treatment modalities such as antiviral drugs have shown only limited success. By some estimates AIDS has reached epidemic proportions. Hence, the AIDS virus, referred to by several names, including lymphadenopathy-associated virus (LAV), human immunodeficiency virus type one (HIV-1) and human T-cell lymphotrophic virus type 3 (HTLV-III), has been studied extensively.

It is now known that HIV-1 is a retrovirus having a characteristic envelope protein, glycoprotein 120. Glycoprotein 120 (gp120) is linked by a transmembrane glycoprotein (gp41) to protein 18 which in turn encloses the viral capsid (protein 24) which houses viral RNA and reverse transcriptase. HIV-1 preferentially infects helper-inducer T-lympocytes by recognizing a receptor site provided by a surface antigen known as CD4 or T4 and then binding to these T4+lymphocytes. HIV enters the target cell, losing its envelope and releasing the contents of its capsid into the cell cytoplasm. The virus replicates within the infected lymphocyte and new viruses are formed which bud from the cell memberane. It has been demonstrated that gp120 is uniformly expressed by HIV and that substantially all infected subjects produce antibodies to gp120. It has also been shown that those portions of gp120 which recognize and bind T4 cells are highly conserved. Moreover infected T4+lymphocytes express gp120 on their surfaces, providing an important molecular marker for HIV infected T4 lymphocytes. Other cells such as monocytes have also been shown to include T4+sub-populations which bind to HIV gp120, although the precise role of HIV-infected monocytes in AIDS is still unclear.

It would be desirable to provide a method and apparatus by which a preselected virus, virally infected cells, or other pathogenic agent could be removed from a fluid such as blood to reduce or eliminate host infection. It would also be desirable to provide such a method and apparatus which would operate on a continuous flow basis. The present invention achieves these goals.

SUMMARY OF THE INVENTION

In one aspect, the present invention provides a method for removing a preselected pathogenic agent from a fluid. In this embodiment, the invention includes the steps of contacting a fluid containing a preselected pathogenic agent in a mixer with a plurality of paramagnetic beads. The paramagnetic beads have an outer coating that selectively binds to a predetermined antigenic determinant expressed by the pathogenic agent. Preferably, the fluid and coated paramagnetic beads are mixed or agitated in the mixer for a period of time sufficient to cause the beads, by virtue of their coating, to bind to the pathogenic agent. That is, the bead coating binds to the predetermined antigenic determinant to form a pathogenic agent/paramagnetic bead complex. Typically, the fluid will contain a plurality of the preselected pathogenic agent such that a number of complexes will be formed. The fluid containing these complexes is then flowed through a magnetic separator where each complex is restrained against the forward flow in the following manner. A magnetic field is generated in the magnetic separator, preferably such that the magnetic induction is transverse to the flow of fluid. The strength of the magnetic field is maintained at a level sufficient to magnetically retain the pathogenic agent/paramagnetic bead complexes in the separator while the purged fluid is flowed out of the separator.

A system for carrying out the method of the present invention is also provided which includes a plurality of paramagnetic beads having affinity coatings which selectively bind to a predetermined antigenic determinant expressed by a preselected pathogenic agent. Means for mixing is provided into which the subject fluid is preferably flowed along with the paramagnetic beads. Mixing or agitation of the liquid and coated paramagnetic beads in the mixing means is carried for a period sufficient to contact and bind each unit of pathogenic agent with paramagnetic beads to form a complex. The mixing means forms one component of a flow circuit which includes pump means or the like for flowing the fluid through the circuit. Another component of the flow circuit, means for magnetically separating the complexes from the fluid, receives the fluid and entrained complexes from the mixing means. In one embodiment, this magnetic separator means includes a tube through which the fluid is flowed. A magnetic field generator generates a magnetic field which penetrates the tube, transverse to the flow of fluid. This transverse magnetic field draws the paramagnetic beads and bound pathogen to the tube walls where they are retained by the magnetic force. Thus, the paramagnetic beads and bound pathogen are retained in the magnetic separator while the purged fluid continues to flow through and out of the magnetic separator.

The apparatus of the present invention is preferably utilized to carry out the method of the present invention in a continuous flow manner such that it can be used to continuously purge blood. In this embodiment, blood is flowed out of the body through a cannula or the like. An anticoagulant is added to the blood to prevent clotting during contact with circuit elements which are encountered during the purging process. The blood is pumped through the cannula to a suitable mixer such as a mixing coil. Coated affinity beads or microspheres are added to the blood, preferably before the blood enters the mixing coil. Blood is preferably flowed through the circuit by peristaltic pumps or the like. As the blood and paramagnetic beads move through the mixing coil, sufficient mixing and agitation take place for the paramagnetic beads to bind to preselected targets such as HIV virus or infected T-4 lymphocytes. As the blood leaves the mixing coil, substantially all of the pathogenic agent to be removed is bound by paramagnetic beads.

The blood with the entrained complexes is then flowed through a magnetic separator which includes a tube in flow communication with the mixing coil. The paramagnetic bead/pathogenic agent complexes are retained in the separator, again by applying a magnetic field which penetrates the separator tube to magnetically bind complexes to the tube wall. Since the complexes are magnetically adhered to the tube, they are retained within the separator as blood continues to flow through and out of the separator, substantially purged of the preselected pathogenic agent. The purged blood is then flowed back into the body. The method and apparatus of the present invention may be used for purging the blood of humans or animals.

A pressure sensor is also preferably provided to keep blood flow relatively constant. Access to the subject may include the conventional techniques used in dialysis such as a subcutaneous arteriovenous fistula or an artificial fistula and the like.

These and other aspects of the present invention will be more fully described in the description of the preferred embodiment with reference to the drawings.

DESCRIPTION OF THE PREFERRED EMBODIMENTS

Figure 1:
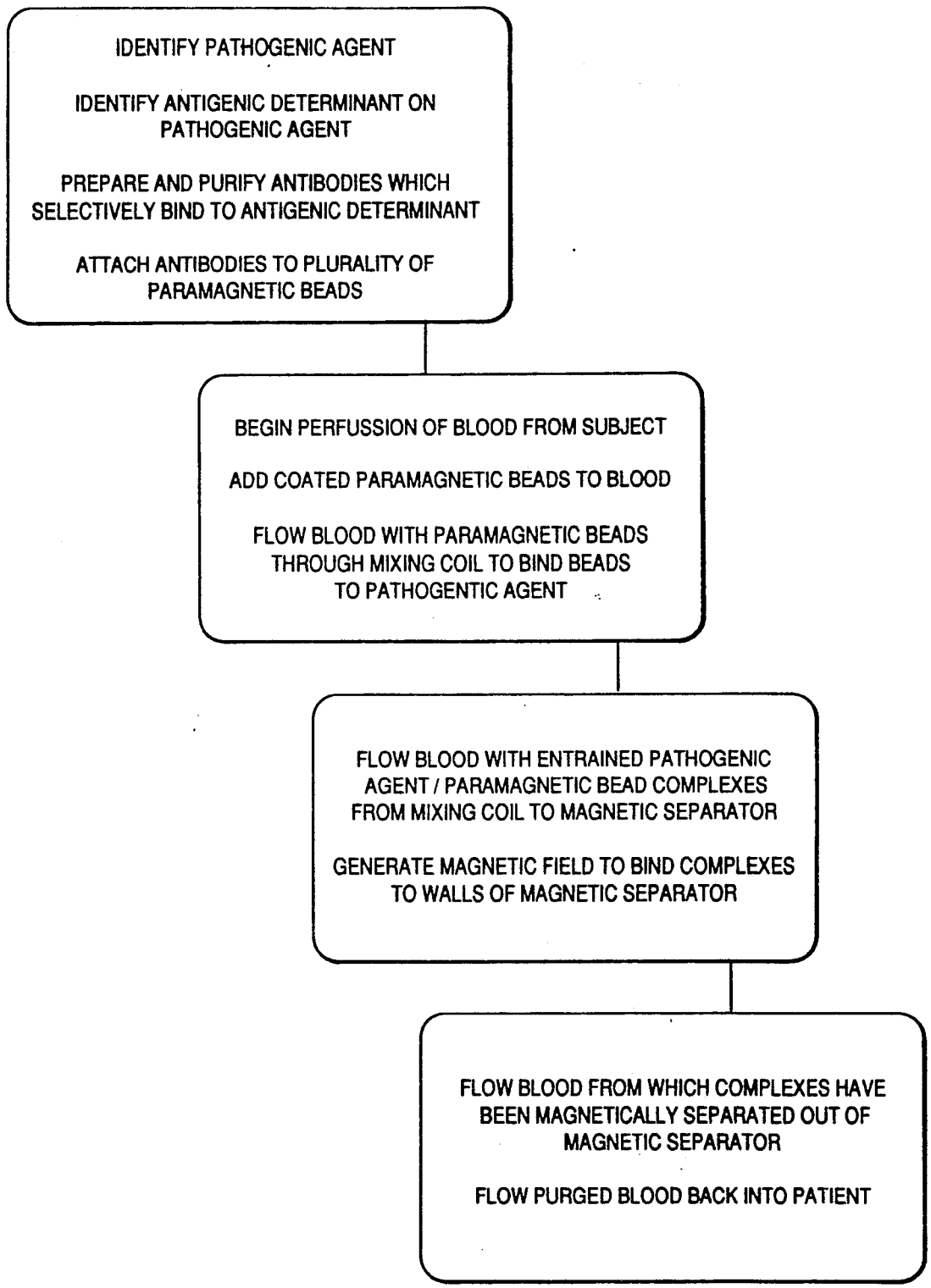
FIG. 1 is a block diagram illustrating the process of the present invention in one embodiment.

With reference now to FIG. 1 of the drawings, the first step of the method of the present invention includes the selection of a preselected pathogenic agent and the identification or selection of an associated antigenic agent. As used herein, the term "pathogenic agent" is defined broadly and includes, without limitation, viruses, virally infected cells, bacteria, and other particles or organisms the presence of which is toxic or otherwise undesirable in a biological host. Preferred pathogenic agents to be removed using the present invention are HIV-1 or HIV-2, and HIV infected T-lymphocytes which are known to be present in subjects afflicted with AIDS. A composition is then prepared for coating a plurality of paramagnetic beads. The composition selectively binds the predetermined antigenic determinant on the preselected pathogenic agent with low and, preferably, substantially no cross-reactivity with other structures. The most preferred composition for use as the paramagnetic bead coating comprises an immunoglobulin or antibody which recognizes and binds selectively to the preselected pathogenic agent. The preferred antibodies for coating the paramagnetic beads of the present invention are high affinity anitibodies which, with respect to the preselected antigenic determinant, have an affinity constant greater than $10^8 M^{-1}$ and preferably greater than $10^{12} M^{-1}$, that is, $K_{aff}(M^{-1})$ is preferably greater than $10^8$ and most preferably greater than $10^{12}$. Suitable polyclonal or monoclonal antibodies which meet these requirements may be prepared for use in the present invention using well-known immunization and purification techniques.

Suitable magnetic or paramagnetic beads utilized in the present invention are commerically available from a number of vendors. Preferred beads provide a large surface area for coupling antibody and have low nonspecific absorbtion of materials. Also, suitable beads should not interfere with the biological activity of the affinity coating. Ideally, the coated paramagnetic beads should disperse well in the fluid in which they will bind the pathogenic agent. The paramagnetic beads most preferably include an iron oxide core, the surface of which is functionalized so that immunoglobulins can be covalently attached. Other materials which can be magnetically influenced may be suitable. Preferably, the functional groups of the bead surface are primary amino groups or carboxyl groups. It will be known to those skilled in the art that immunoglobulins can be coupled to either of these functional groups by a number of methods, for example, using the procedures set forth in *Biochem. Biophys. Res. Comm.* 45, 1574 (1971). As stated, the coated paramagnetic beads should remain suspended in the subject liquid and should not aggregate except in response to an applied magnetic field.

Further, the preferred paramagnetic beads should have a sealed surface to minimize the amount of antibody necessary to coat the beads. By "sealed surface" it is meant that the bead surface is relatively smooth rather than irregular. These characteristics insure a maximum and uniform binding surface at all times. Particularly preferred paramagnetic beads are those sold under the trade name "Biomag" which may be obtained from Advanced Magnetics, Inc. Paramagnetic beads of various sizes may be utilized, but it is preferred that the average bead size be from about 0.01 to about 10 microns in diameter and most preferably about 4.5 microns in diameter. Of course, the response of the coated paramagnetic beads to an applied magnetic field will be a function of both the bead size and the nature and size of the paramagnetic core. Most preferred are paramagnetic beads which comprise a monodispersed polystyrene body, for example a polymer of styrene divinylbenzene, into which is incorporated paramagnetic iron oxide such as magnetite ($Fe_3O_4$) where the iron oxide comprises from about 10% by weight to about 40% by weight, and most preferably about 20% by weight of the bead. Other polymers such as dextran, polymethylmethacrylate and copolymers with methacrylic acid or acrylamide having carboxyl and amide functional groups are also suitable along with many other iron-containing latex particles. In one embodiment, it is preferred that an initial or inner coat of a first antibody be applied, with the first immunoglobulin having the capacity to bind both the functionalized bead surface and a second antibody, although it may be suitable to attach the second antibody directly to the functionalized bead surface. The second antibody has the capacity to selectively bind the preselected pathogenic agent. In this embodiment, the first antibody coat is attached to the paramagnetic bead in the described manner and thereafter the pathogenspecific antibody is coupled to this first or inner antibody layer.

It is to be understood that in the present invention, the paramagnetic bead coating covers substantially all of the functionalized surface of the bead so that upon contact with a complimentary binding site on a pathogenic agent the paramagnetic beads will have a high probability of attaching to the pathogenic agent. In the most preferred embodiment, the affinity coating of the preferred paramagnetic beads comprises antibodies which selectively bind to glycoprotein 120 (gp120) as expressed by HIV-1 virus. In another embodiment, the preferred coating includes antibodies which selectively bind to gp120 as expressed by T-4 lymphocytes infected by HIV-1. Antibodies directed to other suitable markers which will be known to those skilled in the art may also be used to selectively bind virus or a cell subpopulation in a fluid such as whole blood or the like. The preferred concentration of antibodies per 100 mg of paramagnetic beads having the preferred characteristics, that is a 20% by weight magnetite in a polystyrene/divinylbenzene matrix, where the bead diameter is about 4.5 microns, is about 2 mg to about 8 mg and most preferably about 3.4 mg of antibodies per 100 mg of beads. The most preferred coating for use in the present invention comprises sheep anti-mouse IgG antibody which is covalently bound directly to the functional groups of the bead polymer. Antibodies against HIV-1 are then attached to the sheep anti-mouse IgG antibody layer at a concentration of about 3.4 mg/100 mg of uncoated paramagnetic beads. Thus, the first step of the invention in one embodiment includes the identification or selection of the pathogenic agent to be removed from a fluid such as blood in which it resides. The antigenic determinant or epitope expressed by the pathogenic agent is then identified or selected. Antibodies which selectively recognize and bind to the predetermined epitope expressed by the preselected pathogenic agent are then produced using conventional immunization techniques. These antibodies are used to coat the preferred paramagnetic beads in one of the aforementioned manners. Antibodies which selectively bind to an antigenic determinant of gp 120 may be obtained commerically from DuPont, which are preferred for use in the present invention. In "Prospects For The Therapeutic Use Of Human Monoclonal Antibodies," *J. Biol. Response Mod*, Vo. 5, No. 5 (1986) a number of antigens are listed against which monoclonal antibodies have been produced which may be desirable for use in the present invention. The present invention is useful in separating a variety of pathogenic agents, including viral and bacterial pathogens, where markers have been identified against which antibodies can be produced.

Figure 2:
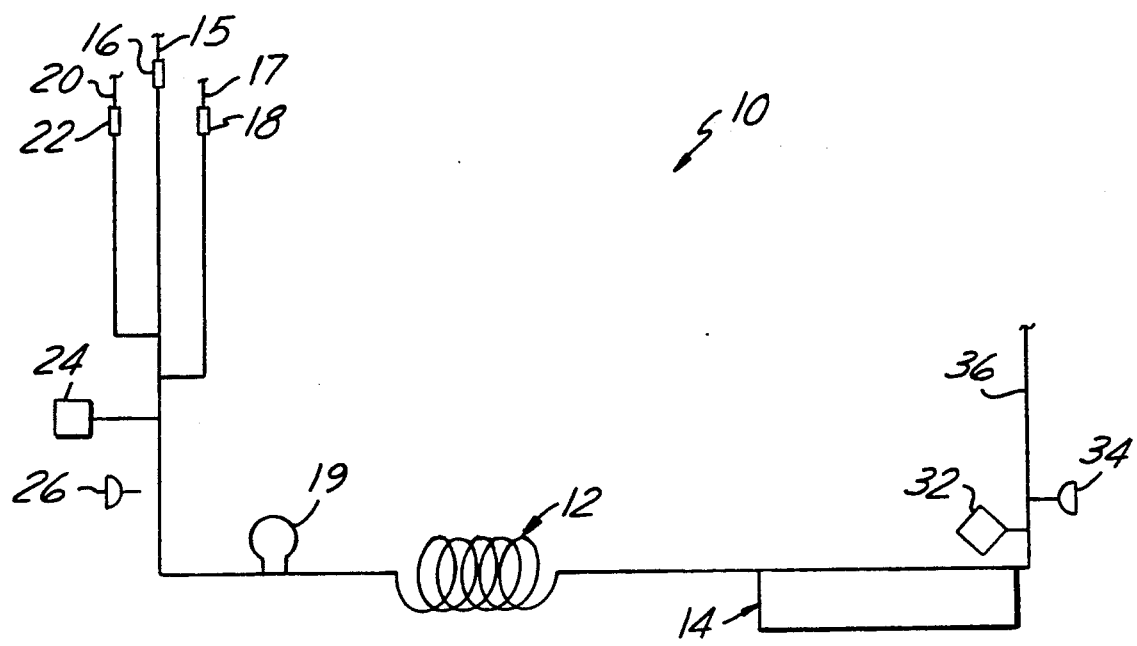
FIG. 2 is a diagrammatic illustration of the apparatus of the present invention.

Referring now to FIG. 2 of the drawings, flow circuit 10 of the present invention is shown generally having mixing coil 12 and magnetic separator 14. The coated paramagnetic beads of the present invention are introduced into blood that contains the pathogenic agent, preferably HIV-1 and/or HIV-1 infected T-lymphocytes, to be removed. In the preferred embodiment, arterial blood is perfused from the brachial artery of a human subject into flow line 15 using a cannula or the like. Blood flow from the subject is controlled initially by valve 16. In this embodiment, and as will be demonstrated more fully herein, the method and apparatus of the present invention provide continuous flow of blood from a biological subject, either human or animal, through flow circuit 10 of the present invention, whereby purged blood is returned to the subject at substantially the same flow rate at which it leaves the subject. The coated paramagnetic beads are preferably metered into the blood via line 17 using valve 18 before the blood enters mixing coil 12, although it may be suitable in some applications to add the coated paramagnetic beads directly to mixing coil 12 such that the coated paramagnetic beads are engulfed by blood as it enters mixing coil 12.

The quantity or number of coated paramagnetic beads which are introduced into the blood will vary depending upon the level of infection. Therefore, the density of pathogenic agent is preferably determined prior to the introduction of coated paramagnetic beads into the blood. This information is preferably obtained using the technique set forth in the aforementioned U.S. patent application Ser. No. 113,589. Of course, where each unit of pathogenic agent expresses multiple copies of a preselected pathogenic determinant, additional paramagnetic beads will be required to ensure that each preselected virus or cell is bound to at least one paramagnetic bead. Where the pathogenic agent comprises infected cells such as HIV infected T-lymphocytes, it is preferred that four magnetic beads be bound to each infected cell and most preferred that a minimum of 10 beads per cell be bound to each infected cell. In HIV-infected patients, approximately 1 in 10,000 to about 1 in 100,000 T-lymphocytes contain virus. Hence, it is preferred that about 100,000 to about 1,000,000 coated paramagnetic beads be introduced per ml of blood. In order to facilitate the introduction and metering of the coated paramagnetic beads into the flow system, it is preferred that a suspension of the beads be prepared. That is, the beads are uniformly dispersed in a fluid. The fluid or carrier comprises a fluid which is physiologically compatible with the subject undergoing treatment such as an isotonic phosphate-buffered saline solution. It is preferred that the solution also contain an effective amount of an antibiotic such as penicillin or ampicillin to reduce any bacterial growth which may be associated with the beads. The solution is also preferably formulated such that it is at physiological pH. In some instances, it may be necessary to agitate the bead suspension as the beads and liquid carrier are introduced in the flow circuit to ensure that the beads are relatively uniformly dispersed in the carrier. If the paramagnetic beads are purchased in a stock solution, they can be isolated by vacuum drying or preferably freeze drying and then added to the aforementioned physiological solution. This provides approximately 1,000 to 10,000 excess beads per ml of blood based on a count of four to ten bound beads per infected cell. With the preferred beads, there are approximately $5 \times 10^8$ beads or particles per ml of bead suspension. Based on the preferred flow rates, the bead suspension is introduced at a rate of about 0.8 microliters to about 2.0 microliters and preferably about 1.2 microliters of bead suspension per minute. Thus, about $6 \times 10^5$ beads are introduced per minute into the blood.

A number of pump means for facilitating the flow of blood through flow circuit 10 are appropriate, but peristaltic pump 19 is preferred. Blood flow rate through flow circuit 10 should be maintained at about 250 cc/min to about 300 cc/min and preferably about 275 cc/min. Mixing coil 12 preferably has the capacity of about 200 ml to about 400 ml, and most preferably about 300 ml. In addition to the subject's blood, an anticoagulant such as heparin in an amount sufficient to inhibit coagulation or clotting of blood as it passes through flow circuit 10 is added to the blood as it flows through flow line 15 into mixing coil 12. Of course, the quantity of anticoagulant or other similar agent which is used to prevent coagulation should not adversely affect the subject. An amount of Heparin effective to substantially prevent unwanted coagulation and which does not produce unwanted physiological side effects should be used. A suitable concentration of Heparin is about 1000 to about 10,000 units per 10 ml blood, where 140 units equal 1 mg of Heparin. It may also be desirable in some applications to first flush the circuit with a salene flushing fluid or the like introduced into flow line 15 via line 20 and valve 22 to remove any contaminants which may be present in the circuit prior to commencing blood flow. It may also be desirable to provide a pressure sensor 24 for sensing the fluid pressure of the blood as it passes through the flow circuit 10 and valves which regulate the flow of blood through the circuit, particularly where the purged blood is reintroduced into the subject's body. Further, a siphon tube or sampling port 26 may be included in flow line 15 to permit the removal of a blood sample for testing. The preferred testing method for use in the present invention is that disclosed in the aforementioned patent application Ser. No. 113,589, the disclosure is which is incorporated herein by reference.

Thus, and with reference to FIG. 1 of the drawings, this step of the invention includes the perfussion of blood from a subject and the introduction of a plurality of the coated paramagnetic beads into the blood along with an anticoagulant. The blood is preferably sampled and tested to detect the presence of the preselected pathogenic agent at the initiation of blood flow. Also, fluid pressure is preferably determined and controlled throughout flow circuit 10, which helps ensure that no leakage occurs in the system.

Next, blood is flowed into mixing coil 12 for mixing or agitating the blood with the coated paramagnetic beads to promote contacting of the pathogenic agent by the antibody coating. It is important that good mixing or agitation take place to insure that substantially all of the pathogenic agent contacts and is bound by the coated paramagnetic beads. As will be known by those skilled in the art, the probability of binding upon contact and the strength of the bond between the pathogenic agent and the bead coating are functions of the affinity and avidity characteristics of the antibody which forms the bead coat. Preferably, affinity and avidity values should be high to promote rapid and strong binding.

Figure 4:
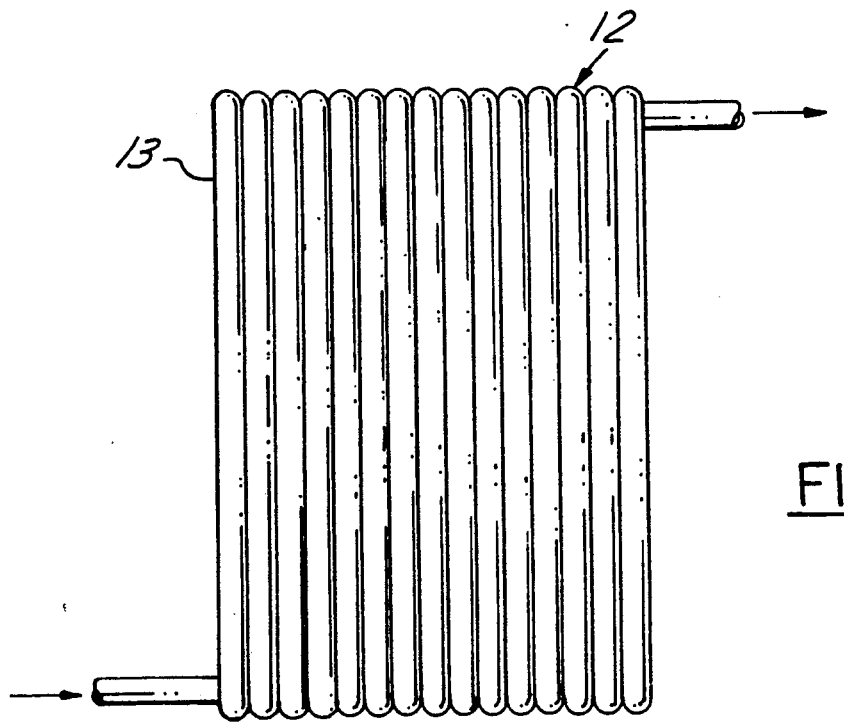
FIG. 4 depicts a preferred mixing coil in side elevational view for use in the present invention.

Referring now to FIG. 4 of the drawings, the preferred mixing coil 12 comprises a tubular coil through which the beads and blood are flowed under pressure. Tube 13 which is used to form mixing coil 12 is preferably about 200 cm to about 500 cm in length and most preferably 300 cm in length. Tube 13 preferably has an internal diameter of from about 0.5 cm to about 1.5 cm and most preferably about 1 cm. Mixing coil 12 provides excellent mixing characteristics in the present invention. Mixing coil 12 may include recirculating shunts or the like. As stated, the volumetric capacity of mixing coil 12 is about 200 ml to about 500 ml and preferably about 300 ml. The coated paramagnetic beads or microspheres and blood are mixed sufficiently to substantially bind all of the pathogenic agent present in the blood as it flows through the mixer. Also, it is to be understood that although the number of coated paramagnetic beads which are introduced into the blood is preferably in excess of the number required to substantially bind all of the pathogenic agent present in the blood, the beads should not be added at a rate which interferes with blood flow through the various circuit elements.

In the next step of the invention, and referring again to FIGS. 1 and 2 of the drawings, blood is flowed out of mixing coil 12 with substantially all of the pathogenic agents such as the HIV-1 virus or HIV-1 infected T-lymphocyte cells having one or more coated paramagnetic beads bound to its surface at the preselected antigenic determinant. Thus, blood containing these paramagnetic beads/pathogenic agent complexes is flowed out of mixing coil 12 and into means for magnetically removing or restraining the paramagnetic beads/pathogenic agent complex, illustrated in FIGS. 2 and 3 as magnetic separator 14.

Figure 3:
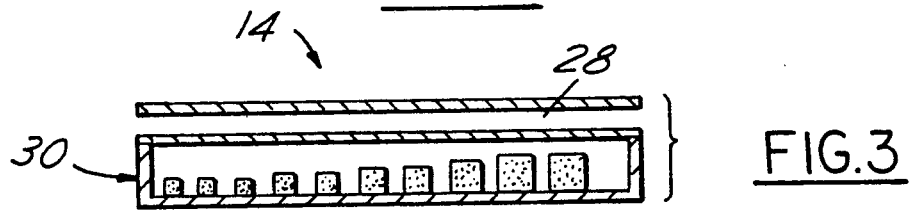
FIG. 3 is a cross-sectional, side elevational view of the preferred magnetic separator of the present invention.

As shown in FIGS. 1 and 3, next the blood in which the paramagnetic beads/pathogenic agent complexes are entrained is flowed into a separation chamber 28 which in this embodiment is a flat elongated tube. The volumetric capacity of separation chamber 28 is about 200 ml to about 500 ml and preferably about 300 ml. Adjacent separation chamber 28 and forming part of magnetic separator 14 is a magnetic field generator 30 such as a series of permanent magnets or an assembly of electromagnetics which preferably may be activated to produce a graded magnetic field along the length of separation chamber 28. The blood with the paramagnetic bead/pathogenic agent complexes first enter separation chamber 28 where a weak magnetic field is generated by field generator 30 sufficient to penetrate the walls of separation chamber 28 and to adhere at least a portion of the complexes to the separation chamber wall. In this fashion, the complexes are restrained against the continuous forward flow of blood through separation chamber 28. Paramagnetic bead/pathogenic agent complexes which are not drawn to the chamber wall by this weak magnetic field, which may result from the position of the complexes in the blood relative to other blood constituents, are carried along further in the blood through separation chamber 28 where they are then acted upon by a stronger magnetic field. That is, by providing a graded magnetic field along the length of separation chamber 28, substantially all of the paramagnetic bead/pathogenic agent complexes become magnetically adhered or attached to the separation chamber wall where they are restrained against the forward flow of blood out of separation chamber 28. Thus, as the blood exits separation chamber 28, substantially all of the paramagnetic bead/pathogenic agent complexes have been magnetically removed from the blood. To confirm that no paramagnetic beads leave the separation chamber with the purged blood, a photosensor 32 or a similar bead detector is preferably provided in flow circuit 10 following separation chamber 28. When sensor 32 detects a bead, sensor 32 activates a shunt or shut down of the system so that the bead does not enter the subject's circulatory system. The detector is preferably a particle size analyzer such as that which can be obtained from Munhall Company under the trade name "Labtech 100". Of course, the presence of paramagnetic bead/pathogenic agent complexes also indicates incomplete separation in magnetic separator 14. It may also be desirable to provide two separation chambers (not shown) in side-by-side relationship and a directional valve system which alternates flow of blood containing the paramagnetic bead pathogenic agent complexes between the chambers to allows magnetically adhered complexes to be flushed out of one separation chamber while more complexes are collected in the other chamber. In other words, blood can be intermittently channeled between the two separation chambers to allow cleaning of the separation chambers without disrupting blood flow through the circuit.

It will be understood that the present invention collects pathogens in the magnetic separator. Thus, it may be useful in detecting the presence of pathogens having low titers which may not be detectable using conventional assays.

In more detail, and with reference again to FIG. 3 of the drawings, magnetic separation chamber 28 preferably comprises a flat rectangular tube of a non-magnetic material having a bore or chamber of from about 200 cm to about 400 cm in length, and most preferably about 300 cm in length, from about 0.5 cm to about 1.5 cm in height, preferably about 1 cm, and from about 0.5 to about 1.5 cm in width, preferably about 1.0 cm. The magnetic field is graded along separation chamber 28 such that it begins at about 3,500 to about 4,500 Gauss, most preferably about 4,000 Gauss and increases to about 9,500 to about 10,000 Gauss, most preferably about 10,000 Gauss. A magnetic flux density too large may shear the bead from the pathogenic agent.

Finally, when the blood leaves magnetic separator 14 it is substantially purged of the preselected pathogenic agent. To verify that the blood has been adequately purged, a second siphon tube or sampling port 34 is provided in flow circuit 10 following magnetic separator 14. Flow line 36 is provided which leads directly into the subject such that the entire system is a continuous flow circuit similar to that used in blood dialysis systems. The flow rate of blood through flow circuit 10 should be maintained at about 40 to about 100 and preferably about 60 ml/minute. Preferably, the purged blood will be returned to the venous system port of the subject. Where approximately 5 to 6 liters of blood is processed, preferably only about 600 to 700 ml will occupy flow circuit 10 at any given time. The purging process should be completed in approximately 6 to 10 hours of operation.

Where HIV-1 infected T-cells are the pathogen to be removed, marginal intravascular T-cells may be demarginalized with cortisone or epinephrin injections prior to processing such that these infected T-cells enter the peripheral blood to be processed in the manner described. Also, it should be pointed out that infected T-4 lymphocytes which reside in connected tissue are believed to be of no consequence in AIDS since they presumably die in situ and are phagocytized without affecting adjacent uninfected tissues.

In still another embodiment of the present invention, coated biodigestable paramagnetic beads made from dextran rather than from styrene divinylbenzene may be injected directly into the subject's circulatory system. In this embodiment, as in the previous embodiments, the paramagnetic beads are coated with the preferred antibody directed against a preselected pathogenic agent. The coated paramagnetic beads are injected directly into the subject where they are mixed during the normal circulation of the subject's blood. That is, they mix with the blood in the subject and bind their target while still in the subject. The arterial blood carrying the complexes is then directed from the brachial artery directly through the magnetic separator of the present invention without first passing through the mixer. The other aspects of the invention in this embodiment are the same as previously described.

It is to be understood that the method and apparatus of the present invention may also be used to remove or separate tumor cells which carry specific surface antigens. Also, certain pathogenic antibodies such as antinuclear antibodies indicated in Lupus, may also be removed from the peripheral blood supply using the method and apparatus of the present invention.

EXAMPLE

In order to further described the present invention, the following example has been provided. It is to be understood that this example is not intended to limit to scope of the present invention in any manner.

A pathogenic agent, such as HIV-1 would be chosen to be separated from a bodily fluid, in this instance blood. Antibodies which selectively bind to an antigenic determinant of a surface protein, for example gp 120, on the virus coat would be obtained from a vendor or it could be prepared using conventional techniques. The $K_{aff}(M^{-1})$ would be $10^{12}$ with respect to the HIV-1 determinant. Paramagnetic beads having iron oxide cores would then be provided. The paramagnetic beads would have an average diameter of 4.5 microns and would have a surface functionalized with primary amino groups. The beads would then be coated with the aforementioned antibodies by coupling the antibodies to the functional groups on the bead surface in the conventional manner. Substantially all of the bead surface would be covered by the antibodies. 5.0 mg of antibody would be applied to each 100 mg of beads. A "suspension" of the coated paramagnetic beads should then be prepared by introducing the coated beads into an isotonic phosphate-buffered saline solution to a concentration of about $5.0 \times 10^8$ beads per milliliter of saline solution.

A flow circuit would then be provided which includes a peristaltic pump to move blood through the system. Blood would be flowed from a biological subject using a cannula and would then be pumped by the peristaltic pump into a mixing coil having a capacity of 300 ml. Heparin would be added to the blood as it is flowed out of the biological subject to prevent coagulation. It will be understood that for an individual subject, an effective amount of heparin for anticoagulation purposes can be determined by conventional coagulation assays prior to initiation of treatment by the present invention. Heparin would be added gradually to provide a heparin concentration of about 5000 standard units per 15 ml of blood; that is, roughly 2.5 mg heparin per milliliter of blood. A blood sample from the subject would be tested to determine the level of infectivity to be used as a reference in determining the quantity of HIV-1 to be removed by the present invention. The mixing coil would be a tubular coil of a 300 cm tube length. The tube would have an internal diameter of 1 cm. The coated paramagnetic beads would then be introduced into the blood just before the blood enters the mixing coil. Beads would be introduced into the blood at a rate of about $6 \times 10^5$ beads/min., which is about 1.2 microliters of the bead suspension per minute. The blood flow through the mixing coil would be 60 ml per minute. The blood in the paramagnetic beads would mix thoroughly as they travel through the mixing coil with a plurality of the paramagnetic beads binding to the HIV antigenic determinant. The blood, excess paramagnetic beads, and HIV-1 virus having bound paramagnetic beads would then be flowed continuously out of the mixing coil into a magnetic separator. The magnetic separator would be a flat rectangular tube, having a bore 300 cm in length, 1 cm in height, and 1 cm in length with a volumetric capacity of 300 cc. The tube would be made of a non-magnetic material with the tube wall measuring several millimeters in thickness and would have an array of magnets attached to the bottom of the tube. The array of magnets would be graded such that at the beginning of the tube the flux density would be 4,000 Gauss and would increase along the tube to the end of the tube where the flux density would be 10,000 Gauss. As the blood, excess beads, and bead-virus complexes flowed into the separator, the beads and bead-virus complexes would be magnetically drawn to the bottom of the tube where they would remain while the purged blood would continue to flow through the seperator. The purged blood would then be flowed out of the separator and would be analyzed to verify that both the paramagnetic beads and the pathogenic agent had been sufficiently removed from the blood. When the blood was sufficiently purged it would be reintroduced into the subject.

While a particular embodiment of this invention is shown and described herein, it will be understood of course, that the invention is not to be limited thereto since many modifications may be made, particularly by those skilled in the art, in light of this disclosure. It is contemplated therefore by the appended claims to cover any such modifications as fall within the true spirit and scope of this invention.

What is claimed is:

1. A method for the substantially continuous-flow purification of whole blood by removing preselected cells or viruses from said blood, consisting essentially of the steps of:

substantially continuously flowing blood from a human subject through a mixing means, said blood being contaminated with preselected cells or viruses;

introducing from about 100,000 to about 1,000,000 paramagnetic beads per milliliter of said blood into said blood as said blood is flowed into said mixing means, said paramagnetic beads having a coating of antibodies which selectively bind to substantially only said cells or viruses, said paramagnetic beads having an average diameter of from about 0.01 microns to about 10.0 microns;

mixing said blood and said paramagnetic beads as said blood and said paramagnetic beads are flowed through said mixing means such that said paramagnetic beads contact and bind to said cells or viruses to form paramagnetic beads complexed with said cells or viruses;

flowing said blood having said paramagnetic beads complexed with said cells or viruses from said mixing means to means for magnetically restraining said paramagnetic beads complexed with said cells or viruses;

magnetically restraining said paramagnetic beads complexed with said cells or viruses in said magnetic restraining means while flowing said blood through said magnetic restraining means;

flowing said blood out of said magnetic restraining means while retaining said paramagnetic beads complexed with said cells or viruses in said magnetic restraining means such that said blood is purified by the removal of said cells or viruses; and flowing said purified blood into said subject.

2. A method as defined in claim 1, wherein the paramagnetic beads complexed with said cells or viruses are discarded after the purified blood is returned to said subject.

* * * * *